United States Patent [19]

Cadiergue et al.

[11] Patent Number: 4,939,172
[45] Date of Patent: Jul. 3, 1990

[54] NOVEL CYCLOPROPANE CARBOXYLATES

[75] Inventors: Joseph Cadiergue, Bois; Jácques Demassey, Montevrain; Jean-Pierre Demoute, Montreuil-sous-Bois; Jean Tessier, Vincennes, all of France

[73] Assignee: Roussel Uclaf, Paris, France

[21] Appl. No.: 153,157

[22] Filed: Feb. 8, 1988

[30] Foreign Application Priority Data

Feb. 6, 1987 [FR] France .................. 87-01458

[51] Int. Cl.$^5$ .................. C07C 255/33; A01N 37/34; A01N 53/00
[52] U.S. Cl. .................. 514/531; 546/290; 548/187; 548/225; 549/66; 556/441; 558/408; 558/409; 558/410; 558/414; 560/124; 568/55; 568/639; 568/775
[58] Field of Search ............... 560/124; 514/531, 521; 558/408, 414

[56] References Cited

U.S. PATENT DOCUMENTS

| | | | |
|---|---|---|---|
| 4,370,346 | 1/1983 | Punja | 514/531 |
| 4,405,640 | 9/1983 | Punja | 514/531 |
| 4,459,305 | 7/1984 | Katsuda et al. | 548/530 X |
| 4,489,093 | 12/1984 | Martel et al. | 514/351 X |

FOREIGN PATENT DOCUMENTS

| | | |
|---|---|---|
| 0041021 | 3/1982 | European Pat. Off. ............ 514/531 |
| 0050534 | 4/1982 | European Pat. Off. . |
| 0031199 | 12/1983 | European Pat. Off. . |
| 0038271 | 7/1984 | European Pat. Off. . |
| 0048186 | 5/1985 | European Pat. Off. . |
| 2171994 | 9/1986 | United Kingdom . |

OTHER PUBLICATIONS

British Crop Protection Conference-Pests and Diseases, -1986, 3B-1, pp. 199-206, McDonald et al., author.

Primary Examiner—Joseph Paul Brust

Attorney, Agent, or Firm—Bierman & Muserlian

[57] ABSTRACT

Novel cyclopropane carboxylic acid esters of all possible stereoisomeric forms and mixtures thereof of the formula

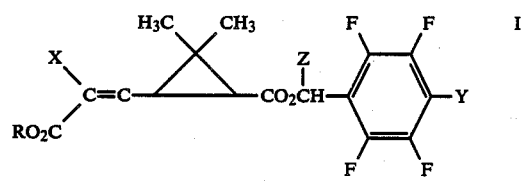

wherein X is selected from the group consisting of hydrogen, fluorine, chlorine and bromine, R is selected from the group consisting of optionally unsaturated alkyl of 1 to 8 carbon atoms optionally substituted, optionally unsaturated cycloalkyl of 3 to 8 carbon atoms optionally substituted, optionally substituted aryl of 6 to 14 carbon atoms and optionally substituted heterocycle, Z is selected from the group consisting of hydrogen, —CH$_3$, —CN and —C≡CH and Y is selected from the group consisting of hydrogen, —OH, optionally unsaturated alkyl of 1 to 8 carbon atoms optionally substituted, —CN, —(CH$_2$)$_m$—OAlk, —(CH$_2$)$_m$—S—Alk,

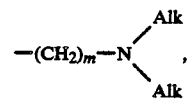

m is 0,1,2,3 or 4, Alk is alkyl of 1 to 12 carbon atoms, —Si(Alk')$_3$, Alk' is optionally unsaturated alkyl of 1 to 8 carbon atoms optionally substituted, —O—Ar and —(CH$_2$)$_m$—Ar and Ar is aryl of 6 to 14 carbon atoms having excellent pesticidal activities and novel intermediates.

23 Claims, No Drawings

NOVEL CYCLOPROPANE CARBOXYLATES

STATE OF THE ART

Various esters of acids of the formula

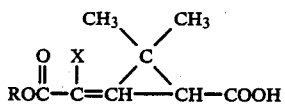

are described in European patent Nos. 0,038,271, 0,041,021, No. 0,048,186 and No. 0,050,534. Alcohols of the formula

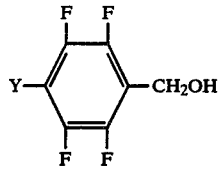

are described in U.S. Pat. Nos. 4,370,346 and 4,405,640, EPO application No. 0,031,199, British patent No. 2,171,994 and British Crop Protection Conference Pest and Disease, 1986, p. 199.

OBJECTS OF THE INVENTION

It is an object of the invention to provide the novel compounds of formula I and a process and novel intermediates for their preparation.

It is another object of the invention to provide novel pesticidal compositions and a novel method of combatting pests.

These and other objects and advantages of the invention will become obvious from the following detailed description.

THE INVENTION

The novel compounds of the invention are cyclopropane carboxylic acid esters of all possible stereoisomeric forms and mixtures thereof of the formula

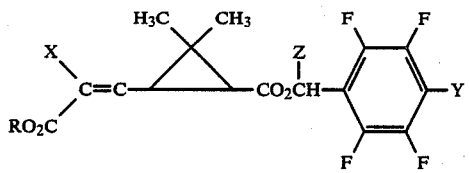

wherein X is selected from the group consisting of hydrogen, fluorine, chlorine and bromine, R is selected from the group consisting of optionally unsaturated alkyl of 1 to 8 carbon atoms optionally substituted, optionally unsaturated cycloalkyl of 3 to 8 carbon atoms optionally substituted, optionally substituted aryl of 6 to 14 carbon atoms and optionally substituted heterocycle, Z is selected from the group consisting of hydrogen, —CH$_3$, —CN and —C≡CH and Y is selected from the group consisting of hydrogen, —OH, optionally unsaturated alkyl of 1 to 8 carbon atoms optionally substituted, —CN, —(CH$_2$)$_m$—OAlk, —(CH$_2$)$_m$—S-Alk,

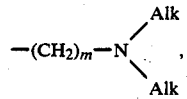

m is 0,1,2,3 or 4, Alk is alkyl of 1 to 12 carbon atoms, —Si(Alk')$_3$, Alk' is optionally unsaturated alkyl of 1 to 8 carbon atoms optionally substituted, —O—Ar and —(CH$_2$)$_m$—Ar and Ar is aryl of 6 to 14 carbon atoms.

When R is saturated alkyl, it is preferably methyl, ethyl, n-propyl, isopropyl, n-butyl, sec-butyl, isobutyl, n-pentyl, n-hexyl, tert-butyl, tert-pentyl or neopentyl. When R is cycloalkyl, it is preferably cyclopropyl, cyclobutyl, cyclopentyl or cyclohexyl or cycloalkylalkyl such as cyclopropyl, cyclobutyl, cyclopentyl or cyclohexyl substituted by at least one of alkyl of which the linkage with the —COO-group is located at any one of its positions, for example 1-methylcyclobutyl, 1-methylcyclopentyl, 1-methylcyclohexyl or 2,2,3,3-tetramethylcyclopropyl. When R is unsaturated alkyl, it is an ethylenic such as, for example, vinyl or 1,1-dimethylallyl, or an acetylenic such as ethynyl or propynyl.

When R is alkyl substituted with at least one functional group, "alkyl" preferably contains 1 to 8 carbon atoms such as methyl, ethyl, propyl, isopropyl, n-butyl,isobutyl or tert-butyl. When R is alkyl substituted with at least on functional group , "functional group" preferably refers to halogen, OR' or SR' in which R' is hydrogen or alkyl of 1 to 8 carbon atoms,

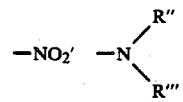

in which R'' and R''' are individually hydrogen or alkyl of 1 to 8 carbon atoms, a —C≡N, HSO$_3$ or H$_2$PO$_4$ or —COAlk$_1$, SO$_2$Alk$_2$ or SO$_3$Alk$_3$ in which Alk$_1$, Alk$_2$ and Alk$_3$ are alkyl of 1 to 18 carbon atoms.

R may also be alkyl substituted with aryl such as benzyl or phenethyl which may optionally be substituted with at least one —OH, —OAlk, or Alk of 1 to 8 carbon atoms, with one or more halogens or —CF$_3$, —OCF$_3$ or —SCF$_3$ or by a group (G):

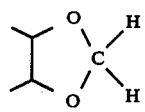

(G)

R may also be alkyl substituted on two adjacent carbon atoms with a group (G$_1$):

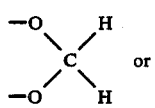

(G$_1$)

or substituted with a group

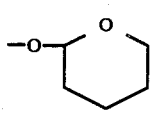

When R is alkyl substituted with one or more functional groups, examples of preferred groups are —(CH$_2$)$_n$C Hal$_3$ in which n is an integer from 1 to 8 and Hal is halogen, for example —CH$_2$CCl$_3$, —CH$_2$CF$_3$, —CH$_2$CH$_2$CCl$_3$ or —CH$_2$—CH$_2$CF$_3$ —(CH$_2$)$_{n1}$CH Hal$_2$ in which Hal is defined as above and $n_1$ is a number of 0 to 8, for example —CH$_2$CHCl$_2$, —CH$_2$CHF$_2$ or —CHF$_2$, —(CH$_2$)$_n$ Hal in which n and Hal are defined as above, for example —CH$_2$CH$_2$Cl or =CH$_2$CH$_2$F, —C(CHal$_3$)$_3$ in which hal is defined as above, for example —C(CF$_3$)$_3$ or

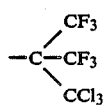

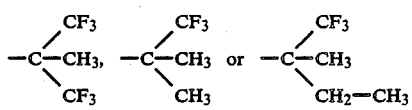

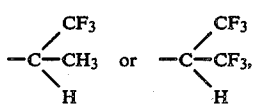

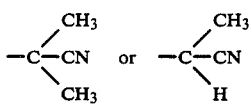

or —(CH$_2$)$_n$CN, in which n is defined as above, for example

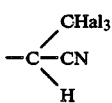

in which Hal is defined as above, for example

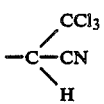

—(CH$_2$)$_n$OR', in which n is defined as above and R' is hydrogen or alkyl of 1 to 8 carbon atoms, for example —CH$_2$OCH$_3$', —CH$_2$CH$_2$OCH$_3$, —CH$_2$CH$_2$—OCH$_2$CH$_3$ or —CH$_2$CH$_2$OH, in which n and R' are defined as above and the two R' radicals may be different from each other, for example

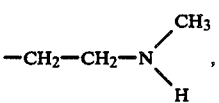

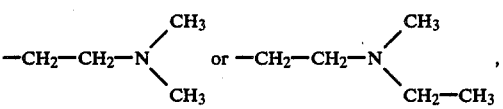

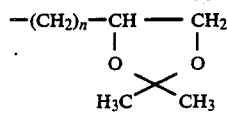

in which n is defined as above, for example

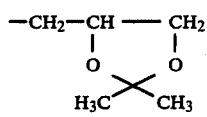

—(CH$_2$)$_n$—CH—CH$_2$
       |     |
       OH   OH in which n is defined as above, for example

—CH$_2$—CH—CH$_2$—OH
       |
       OH

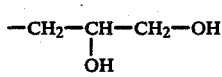

in which n is defined as above, for example

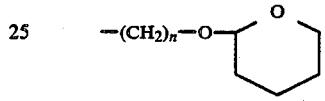

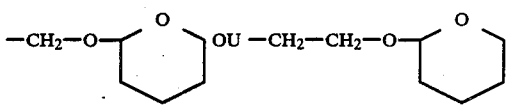

in which n is defined as above, for example benzyl or phenethyl

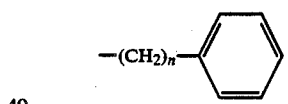

in which n is defined as above, for example

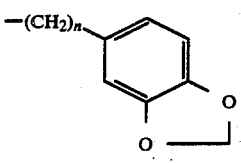

When R is an optionally substituted aryl, it is preferably phenyl or phenyl substituted with one or more OH or Oalk groups, alk having 1 to 8 carbon atoms, or with halogen or —CF$_3$, —OCF$_3$ or —SCF$_3$.

When R is a heterocyclic, it is preferably pyridinyl, furanyl, thiophenyl, oxazolyl or thiazolyl.

In the definition of Y, when it is alkyl it is preferably methyl, ethyl, propyl, isopropyl, n-butyl or tert-butyl. When Y is an unsaturated alkyl, it is an ethylenic radical such as ethenyl, propenyl or propadienyl or an acetylenic such as ethynyl or propynyl. When Y is alkyl substituted with one or more functional groups, "functional group" preferably refers to halogens such as fluorine or bromine. When Y is O-aryl or $-(CH_2)_m$ aryl, "aryl" preferably is phenyl.

Compounds in which X is fluorine, and among these, those in which the geometry of the double bond is E, more specifically form the subject of the invention. Compounds of formula I in which X is hydrogen, and among these, those in which the geometry of the double bond is Z, also form the subject of the invention.

Among the preferred compounds of the invention, are those of formula I in which R is saturated alkyl of 1 to 4 carbon atoms, those in which Z is hydrogen and those in which Y is $CH_3$ or $(CH_2)_mOCH_3$, m is number 0 or 1 or $Ch_2CH=CH_2$.

Among the specific preferred compounds of formula I are 4-Methoxy-2,3,5,6-tetrafluoro-benzyl 1R[1α, 3α, (Z)]-2,2-dimethyl-3-(3-methoxy-3-oxo-1-propenyl)-cyclopropanecarboxylate; 4-Methyl-2,3,5,6-tetrafluorobenzyl 1R[1α, 3α, (E)]-2,2-dimethyl-3-(2-fluoro-3-ethoxy-3-oxo-1-propenyl)cyclopropane-carboxylate; 4-Methyl-2,3,5,6-tetrafluoro-benzyl 1R[1α, 3α(E)]-2,2-dimethyl -3-[3-(1,1-dimethylethoxy)-3-oxo-2-fluoro-1-propenyl]cyclopropane carboxylate; 4-(2-Propenyl)-2,3,5,6-tetrafluoro-benzyl [1R, (1α, 3α)(E)]2,2-dimethyl-3-(3-ethoxy-2-fluoro-3-oxo-1-propenyl)cyclopropane-carboxylate; 4-Methoxy-2,3,5,6-tetrafluoro-benzyl 1R[1α, 3α,(E)-2,2-dimethyl-3-[2-fluoro-3-(1,1-dimethylethoxy-3-oxo-1-propenyl]cyclopropanecarboxylate; 4-Methoxy-2,3,5,6-tetrafluoro-benzyl 1R[α, 3α,-(E)]-2,2-dimethyl-3-(2-fluoro-3-ethoxy-3-oxo-1-propenyl)cyclopropane carboxylate; 4-Methoxymethyl-2,3,5,6-tetrafluoro-benzyl [1R [1α, 3α,(E)]]2,2-dimethyl-3-(2-fluoro-3-ethoxy-3-oxo-1-propenyl)cyclopropane carboxylate; 4-Methoxymethyl-2,3,5,6-tetrafluoro-benzyl [1R[1α, 3α,(E)]]2,2-dimethyl-3-[3-(1,1-dimethylethoxy-2-fluoro-3-oxo-1-propenyl]cyclopropanecarboxylate; and 4-Methoxymethyl-2,3,5,6-tetra-fluoro-benzyl [1R[1α, 3α, (E)]-2,2-dimethyl-3-[2-fluoro-3-methoxy-3-oxo-1-propenyl)cyclopropanecarboxylate.

The novel pesticidal compositions of the invention are comprised of a pesticidally effective amount of at least one compound of formula I and an inert carrier. The compositions have advantageous properties which enable them to be used in pest control. For example, they may be used for the control of crop pests, indoor pests and parasites of warm-blooded animals. Thus, the compositions of the invention may be used for the control of insects, nematodes and mites which are crop pests or animal parasites. The application of the compositions for the control of crop pests, indoor pests and parasites of warm-blooded animals especially forms the subject of the invention.

The compositions of the invention may therefore be used especially for the control of insects in the agricultural field, for the control, for example, of aphids, larvae of lepidoptera and coleoptera and for the control of soil insects. They are employed at doses of between 10 g and 300 g of active substance per hectare.

The compositions may also be employed for the control of indoor insects, especially for the control of flies, mosquitoes and cockroaches. Additionally, products of formula I are photostable and are not toxic to mammals.

Because of the whole range of these properties, the products of formula I are products which correspond perfectly to the requirements of the modern agrochemical industry and they enable harvests to be protected while protecting the environment.

The compositions containing the compounds of formula I may also be employed for the control of mites and nematodes which are crop pests. The compositions may also be used for the control of mites which are parasites on animals, for example for the control of ticks and especially ticks of the Boophilus species, those of the Hyalomnia species, those of the Amblyomnia species and those of the Rhipicephalus species or for the control of all sorts of scabs and especially sarcoptic scabs, psoroptic scabs and chorioptic scabs.

Insecticidal compositions containing at least one of the products of formula I as the active principle especially form the subject of the invention. These compositions are prepared according to the conventional methods in the agrochemical industry or the veterinary industry or the industry of products intended for animal nutrition. In the compositions intended for agricultural use or for use in buildings, one or more other pesticidal agents may optionally be added to the active substance(s). These compositions may be in the form of powders, granules, suspensions, emulsions, solutions, solutions for aerosols, combustible strips, baits or other preparations conventionally employed for using this type of compound.

In addition to the active principle, the compositions generally contain a vehicle and/or a nonionic surfactant which additionaly provides for a uniform dispersion of the constituent substances in the mixture. The vehicle employed may be a liquid such as water, alcohol, hydrocarbons or other organic solvents, a mineral, animal or vegetable oil, a powder such as talcum, clays, silicates, kieselguhr or a combustible solid. The insecticidal compositions according to the invention preferably contain from 0.005% to 10% by weight of active substance.

According to an advantageous procedure, for use in buildings, the compositions of the invention are used in the form of fumigant compositions. The compositions of the invention may then advantageously consist, as the non-active part, of a combustible insecticidal coil or of an incombustible fibrous substrate. In the latter case, the fumigant obtained after the incorporation of the active substance is placed on a heating device such as an electric emanator. In the case where an insecticidal coil is employed, the inert support may consist, for example, of pyrethrum marc, Tabu powder (or powder of *Machilus Thumbergii* Leaves), pyrethrum stem powder, cedar Leaf powder, wood dust (such as pine sawdust) starch and coconut shell powder. The active substance dose may then be for example from 0.03% to 1% by weight. In the case where an incombustible fibrous support is employed, the active substance dose may then be for example 0.03 to 95% by weight.

The compositions of the invention for use in buildings may also be obtained by preparing an oil which can be sprayed, based on the active principle, or the oil soaking the wick of a lamp and then being subjected to combustion. The concentration of the active principle incorporated into the oil is preferably from 0.03 to 95% by weight.

One or more other pesticidal agents may optionally be added to the insecticidal compositions of the invention such as acaricidal and nematicidal compositions. The acaricidal and nematicidal compositions may especially be in the form of powders granules, suspensions, emulsions or solutions. For acaricidal use for spraying onto leaves, wettable powders containing from 1 to 80% or foliar spray liquids containing from 1 to 500 g/l of active principle are preferably employed. Powders for foliar dusting containing from 0.05 to 3% of active substance may also be employed. For nematicidal use, soil treatment liquids containing from 300 to 500 g/l of active principle are preferably employed. The acaricidal and nematicidal compounds of the invention are preferably employed at doses of between 1 and 100 g of active substance per hectare.

To enhance the biological activity of the products of the invention, it is possible to add conventional synergists employed in similar cases such as 1-(2,5,8-trioxadodecyl)-2-propyl-4,5-methylenedioxybenzene (or piperonylbutoxide) or N-(2-ethylheptyl)bicyclo[2,2,1-]hept-5-ene-2,3-dicarboximide, or piperonyl-bis-2-(2'-n-butoxyethoxy)ethylacetal (or tropital).

The compounds of formula I have an excellent general tolerance, and therefore the products of formula I also form the subject of the invention, especially for the control of diseases caused by ticks and scabs in man and animals. The compositions of the invention are especially used for the preventive or curative control of lice ad for scab control. The compositions of the invention may be administered externally by spraying, by shampooing, by bathing or painting. The compositions of the invention for veterinary use may also be administered by painting onto the dorsal spine by the method called the "pour-on" method.

It may also be pointed out that the products of the invention may also be employed as biocides or as growth regulators.

The compositions of the invenion may also be combinations having insecticidal, acaricidal or nematicidal activity, characterized in that they contain as active substance,on the one hand,at least one of the compounds of formula I and, on the other hand, at least one of the pyrethrinoid esters chosen from the group consisting of esters of allethrolone, 3,4,5,6-tetrahydrophthalimidomethyl alcohol, 5-benzyl-3-furyl-methyl alcohol, 3-phenoxybenzyl alcohols and α-cyano-3-phenoxybenzyl alcohols with chrysanthemic acids, 5-benzyl-3-furylmethyl alcohol esters of 2,2-dimethyl-3-(2-oxo-3-tetrahydrothiophenyl idenemethyl)cyclopropane-1-carboxylic acids, 3-phenoxybenzyl alcohol and α-cyano-3-phenoxybenzyl alcohol esters of 2,2-dimethyl-3-(2,2-dichlorovinyl)cyclopropane-1-carboxylic acids, α-cyano-3-phenoxybenzyl alcohol esters of 2,2-dimethyl-3-(2,2-dibromovinyl)cyclopropane-1-caboxylic acids, 3-phenoxybenzyl alcohol esters of 2-para-chlorophenyl-2-isopropylacetic acids, esters of allethrolones, 3,4,5,6-tetrahydrophthalimidomethyl alcohol, 5-benzyl-3-furyl-methyl alcohol, 3-phenoxybenzyl alcohol and α-cyano-3-phenoxybenzyl alcohols with 2,2-dimethyl3-(1,2,2,2-tetrahaloethyl)cyclopropane-1-carboxylic acids, in which "halo" represents a fluorine, chlorine or bromine atom, it being understood that the compounds (1) may exist in the form of all possible stereoismers as well as acid and alcohol copulae of the pyrethrinoid esters above.

The novel method of combatting pests comprises contacting pests with a pesticidally effective amount of at least one compound of formula I. The application of the compound may be as described above.

The process of the invention for the preparation of the compounds of formula I comprises reacting an acid of the formula

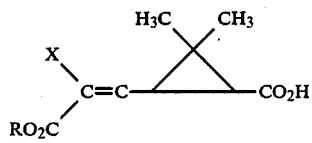

or a functional derivative thereof wherein X and R have the above definition with an alcohol of the formula

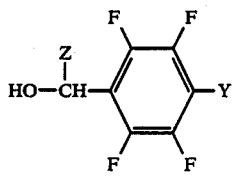

or a functional derivative thereof wherein Y and Z have the above definitions to obtain the corresponding compound of formula I.

The compounds of formula II are known substances described in European Patents No. 0,038,271, No. 0,041,021, No. 0,048,186 and No. 0,050,534. The compounds of formula III in which Z is hydrogen are generally known compounds and they may be prepared for example according to the processes described in European Patent Application No. 0,031,199, in U.S. Pat. Nos. 4,370,346 and 4,405,640, in British Patent No. 2,171,994 or in British Crop Protective Conference Pest and Disease 1986 page 199.

Products of formula III in which Z is other than hydrogen are new products. They may be prepared according to the reaction scheme:

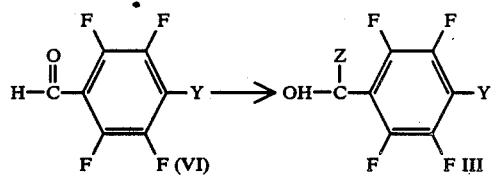

When it is desired to prepare a product of formula III in which Z is methyl, the product of formula VI is reacted with a methyl magnesium halide, for example methyl magnesium iodide. When it is desired to prepare a product of formula III in which Z is C≡N, the product of formula III is reacted with an alkali metal cyanide, for example sodium or potassium cyanide. Some other products of formula III, the preparation of which is given below, are also new products and in themselves form a subject of the present invention.

In a variation of the process, an acid of the formula

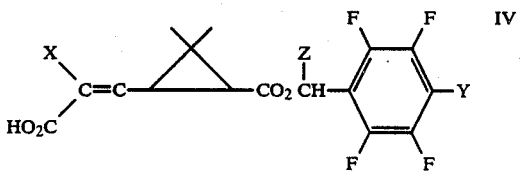

in which X, Y and Z have the above definition is reacted with a alcohol of the formula

ROH            V in which R has the above definition to obtain the corresponding compound of formula I.

In the following examples there are described several preferred embodiments to illustrate the invention. However, it is to be understood tha the invention is not intended to be limited to the specific embodiments.

EXAMPLE 1

1-(4-Methyl-2,3,5,6-tetrafluorophenyl)ethyl 1R[1α (R,S) 3α (E)]-2,2-dimethyl-3-(2-fluoro-3-ethoxy-3-oxo-1-propenyl)cyclopropane-carboxylate 950 mg of dicyclohexylcarbodiimide were introduced at 0 C into a solution of 1 g of 1R[1α (R,S) 3α (E)]-2,2-dimethyl-3-(2-fluoro-3-ethoxy-3-oxo-1-propenyl)cyclopropanecarboxylic acid, 910 mg of α-methyl-4-methyl-2,3,5,6-tetrafluorobenzyl alcohol, 20 ml of methylene chloride and 50 mg of 4-dimethylamino-pyridine. The reaction mixture was stirred for 5 hours at 0 C and the precipitate formed was removed by filtration. The solvent was removed under reduced pressure to obtain 2.12 g of a product which was chromatographed on silica and eluted with a hexane: isopropyl ether (8:2) mixture to obtain 1.6 g of 1-(4-Methyl-2,3,5,6-tetrafluorophenyl)ethyl 1R[1α (R,S) 3α (E)]-2,2-dimethyl-3-(2-fluoro-3-ethoxy-3-oxo-1-propenyl)cyclopropane carboxylate with a specific rotation of $[\alpha]_D = +41 \pm 5°$ (c=1% in $CHCl_3$).

Operating as in Example 1 using the following reaction scheme, the products of Examples 2 to 56 were prepared

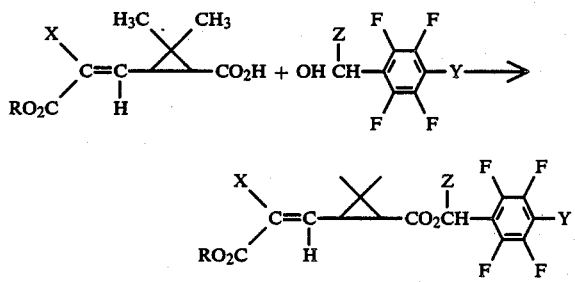

EXAMPLE 2

1-(4-Methyl-2,3,5,6-tetrafluorophenyl)ethyl 1R [1α (R,S) 3α (E)]-2,2-dimethyl-3-[2-fluoro-3-(1,1-dimethylethoxy)-3-oxo-1-propenyl]cyclopropane carboxlate with a specific rotation of $[\alpha]_{D\neq} = +50.5° \pm 1°$ (c+1.3% in $CHCl_3$)

EXAMPLE 3

1-(4-Methyl-2,3,5,6-tetrafluorophenyl)ethyl 1R [1α (R,S) 3α (Z)]-2,2-dimethyl-3-(3-methoxy-3-oxo-1-propenyl)cyclo propanecarboxylate with a specific rotation of $[\alpha]_D = +58° \pm 1°$ (c=1.2% in $CHCl_3$)

EXAMPLE 4

α-Cyano-4-methyl-2,3,5,6-tetrafluoro-benzyl 1R [1α (R,S) 3α (E)]2,2-dimethyl-3-(2-fluoro-3-ethoxy-3-oxo-1-propenyl)cyclopropanecarboxylate with a specific rotation of $[\alpha]_D = +31.2° \pm 1°$ (c=1.3% in $CHCl_3$)

EXAMPLE 5

α-Cyano-4-methyl-2,3,5,6-tetrafluoro-benzyl 1R [1α (R,S) 3α (Z)-2,2-dimethyl-3-(3-methoxy-3-oxo-1-propenyl)cyclo propanecarboxylate with a specific rotation of $[\alpha]hd D = +39° \pm 1.5°$ (c=0.85% in $CHCl_3$)

EXAMPLE 6

α-Cyano-4-methyl-2,3,5,6-tetrafluoro-benzyl 1R [1α (R,S) 3α (E)]-2,2-dimethyl-3-[2-fluoro-3-(1,1-dimethylethoxy) -3-oxo-1-propenylcyclopropanecarboxylate with a specific rotation of $[\alpha]_D = +19° \pm 1°$ (c=1% in $CHCl_3$):

EXAMPLE 7

4-Methyl-2,3,5,6-tetrafluoro-benzyl 1R [1α, 3α (Z)]-2,2-dimethyl-3-3-(3-methoxy-3-oxo-1-propenyl)cyclopropane-carboxylate with a specific rotation $[\alpha]_D = +20° \pm 1°$ (c=0.9% in $CHCl_3$)

EXAMPLE 8

4-Methyl-2,3,5,6-tetrafluoro-benzyl 1R [1α, 3α (E)-2,2-dimethyl-3-(2-fluoro-3-ethoxy-3-oxo-1-propenyl)cyclopropanecarboxylate with a specific rotation $[\alpha]_D = +4° \pm 1°$ (c=0.95% in $CHCl_3$)

EXAMPLE 9

4-Methyl-2,3,5,6-tetrafluoro-benzyl 1R [1α, 3α (E)]-2,2-dimethyl-3-[3-(1,1-dimethylethoxy)-3-oxo-2-fluoro-1-propenyl]-cyclopropanecarboxylate with a specific rotation of $[\alpha]_D = 19.2°$ (c=1.3% in $CHCl_3$)

EXAMPLE 10

4-Methoxy-2,3,5,6-tetrafluoro-benzyl 1R [1α, 3α (Z)]-2,2-dimethyl-3-(3-methoxy-3-oxo-1-propenyl)cyclopropanecarboxylate with a specific rotation of $[\alpha]_D = +17° \pm 1°$ (c=0.75% in $CHCl_3$)

EXAMPLE 11

4-Methoxy-2,3,5,6-tetrafluoro-benzyl 1R [1α, 3α (E)]-2,2-dimethyl-3-[2-fluoro-3-(1,1-dimethylethoxy)-3-oxo-1-propenyl]-cyclopropanecarboxylate melting at 76° C. with a specific rotation of $[\alpha]_D = +13° \pm 1.5°$ (c=0.8% in $CHCl_3$)

EXAMPLE 12

4-Methoxy-2,3,5,6-tetrafluoro-benzyl 1R [1α, 3α(E)]-2,2-dimethyl-3-(2-fluoro-3-ethoxy-3-oxo-1-propenyl)cyclopropanecarboxylate with a specific rotation of $[\alpha]_D = -1.5° \pm 1.5°$ (c=0.75% in $CHCl_3$)

EXAMPLE 13

2,3,5,6-tetrafluoro-benzyl 1R [1α, 3α (E)]-2,2-dimethyl-3-[3-(1,1-dimethylethoxy)-3-oxo-2-fluoro-1-pro penyl]-cyclopropanecarboxylate with a specific rotation of $[\alpha]_D = 22.5° \pm 1°$ (c=1% in $CHCl_3$)

EXAMPLE 14

2,3,5,6-tetrafluoro-benzyl 1R [1α, 3α (Z)]-2,2 dimethyl-3-(3-oxo-3-methoxy-1-propenyl)-cyclopropanecarboxy late melting at 50° C. and with a specific rotation of $[\alpha]_D = +27° \pm 1°$ (c=0.9% in $CHCl_3$)

EXAMPLE 15

2,3,5,6-tretrafluoro-benzyl 1R [1α, 3α (E)]-2,2 ° 1 dimethyl-3-(3-oxo-3-ethoxy-2-fluoro-1-propenyl)-cyclopropane carboxylate melting at 50° C. and with a specific rotation of $[\alpha]_D = -21° \pm 1.5°$ (c=0.7% in $CHCl_3$]

EXAMPLE 16

4-Dimethylamino-2,3,5,6-tetrafluoro-benzyl 1R [1α, 3α (Z)]-2,2-dimethyl-3-(3-oxo-3-methoxy-1-propenyl)-cyclopropane carboxylate with a specific rotation of $[\alpha]_D = +14° \pm 1.5°$ (c=0.7% in CHCl$_3$)

EXAMPLE 17

4-Dimethylamino-2,3,5,6-tetrafluoro-benzyl 1R [1α, 3α (E)]-2,2-dimethyl-3-[3-(1,1-dimethylethoxy)-2-fluoro-3-oxo-1-propenyl]-cyclopropanecarboxylate with a specific rotation of $[\alpha]_D = +9° \pm 1.5°$ (c=0.4% in CHCl$_3$)

EXAMPLE 18

4-Dimethylamino-2,3,5,6-tetrafluoro-benzyl 1R [1α, 3α (E)]-2,2-dimethyl-3-(2-fluoro-3-oxo-3-ethoxy-1-propenyl) cyclopropanecarboxylate with a specific rotation of $[\alpha]_D = -2.5° \pm 2°$ (c=0.6% in CHCl$_3$)

EXAMPLE 19

4-(2-Propenyl)-2,3,5,6-tetrafluoro-benzyl 1R [1α, 3α (E)]-2,2-dimethyl-3-[3-(1,1-dimethylethoxy)-2-fluoro-3-oxo -1-propenyl]cyclopropanecarboxylate with a specific rotation of $[\alpha]_D = +16° \pm 1°$ (c=1% in CHCl$_3$)

EXAMPLE 20

4-(2-Propenyl)-2,3,5,6-tetrafluoro-benzyl 1R [1α, 3α (Z)]2,2-dimethyl-3-(3-oxo-3-methoxy-1-propenyl)cyclopropane carboxylate with a specific rotation of $[\alpha]_D = +6.5° \pm 1°$ (c=1% in CHCl$_3$)

EXAMPLE 21

4-Methoxy-2,3,5,6-tetrafluoro-benzyl 1R [1α, 3α (Z)]-2,2-dimethyl-3-[3-(1,1-dimethylethoxy)-3-oxo-1-propenyl]cyclopropanecarboxylate melting at 60° C. and with a specific rotation of $[\alpha]_D = +27° \pm 1°$ (c=1% in CHCl$_3$)

EXAMPLE 22

4-Methoxy-2,3,5,6-tetrafluoro-benzyl 1R [1α, 3α (E)]-2,2-dimethyl-3-[2-fluoro-3-[2,2,2-(trifluoromethyl)-ethoxy]-3- oxo-1-propenyl]cyclopropanecarboxylate melting at 69° C. and with a specific rotation of $[\alpha]_D = -2° \pm 1°$ (c=1% in CHCl$_3$)

EXAMPLE 23

4-Methoxy-2,3,5,6-tetrafluoro-benzyl 1R [1α, 3α (Z)]-2,2-dimethyl-3-[[3-(2,2,2-trifluoromethyl)-1-(trifluoro methyl)ethoxy]-3-oxo-1-propenyl]-cyclopropanecarboxylate melting at 78° C. and with a specific rotation of $[\alpha]_D = +5.5° \pm 1°$ (c=1% in CHCl$_3$)

EXAMPLE 24

4-Methoxy-2,3,5,6-tetrafluoro-benzyl 1R [1α, 3α (E)]-2,2-dimethyl-3-(2-fluoro-3-methoxy-3-oxo-1-propenyl) cyclopropanecarboxylate with a specific rotation of $[\alpha]_D = +5° \pm 2°$ (c=0.7% in CHCl$_3$)

EXAMPLE 25

4-Ethoxy-2,3,5,6-tetrafluoro-benzyl 1R [1α, 3α(E)]-2,2-dimethyl-3-[3-(1,1-dimethylethoxy)-2-fluoro-3-oxo-1-propenyl]-cyclopropanecarboxylate with a specific rotation of $[\alpha]_D = +24.5° \pm 2°$ (c=0.5% in CHCl$_3$)

EXAMPLE 26

4-Ethoxy-2,3,5,6-tetrafluoro-benzyl 1R [1α, 3α (E)]-2,2,-dimethyl-3-(2-fluoro-3-methoxy-3-oxo-1-propenyl)- cyclo propanecarboxylate with a specific rotation of $[\alpha]_D = +17° \pm 2°$ (c=0.4% in CHCl$_3$)

EXAMPLE 27

4-Methylthio-2,3,5,6-tetrafloro-benzyl 1R [1α, 3α (E)]-2,2-dimethyl-3-(2-fluoro-3-methoxy-3-oxo-1-propenyl)-cyclopropanecarboxylate with a specific rotation of $[\alpha]_D = +1° \pm 2°$ (c=0.5% in CHCl$_3$)

EXAMPLE 28

4-Methylthio-2,3,5,6-tetrafluoro-benzyl 1R [α, 3α-(E)]-2,2-dimethyl-3-(2-fluoro-3-ethoxy-3-oxo-1-propenyl) cyclopropanecarboxylate with a specific rotation of $[\alpha]_D = +4.5° \pm 2°$ (c=0.6% in CHCl$_3$)

EXAMPLE 29

4-Methylthio-2,3,5,6-tetrafluoro-benzyl 1R [1α, 3α-(E)]-2,2-dimethyl-3-[2-fluoro-3-(1,1 -dimethylethoxy)-3- oxo-1-propenyl]-cyclopropanecarboxylate with a specific rotation $[\alpha]_D = +5° \pm 2°$ (c=0.5% in CHCl$_3$)

EXAMPLE 30

4-Difluoromethoxy-2,3,5,6-tetrafluoro-benzyl 1R [1α 3α (E)]-2,2-dimethyl-3-(2-fluoro-3-methoxy-3-oxo-1-propenyl)cyclopropanecarboxylate with a specific rotation of $[\alpha]_D = 20° \pm 1°$ (c=1% in CHCl$_3$)

EXAMPLE 31

4-Difluoromethoxy-2,3,5,6-tetrafluorobenzyl 1R [1α 3α (E)]-2,2-dimethyl-3-[3-(1,1-dimethylethoxy)-2-fluoro-3-oxo-1-propenyl]-cyclopropanecarboxylate with a specific rotation of $[\alpha]_D = +22° \pm 1°$ (c=1% in CHCl$_3$)

EXAMPLE 32

4-Bromodifluoromethoxy-2,3,5,6-tetrafluoro-benzyl 1R [1α, 3α (E)-2,2-dimethyl-3-[3-(1,1-dimethylethoxy)-2-fluoro -3-oxo-1-propenyl]-cyclopropanecarboxylate with a specific rotation of $[\alpha]_D = +16.5° \pm 2°$ (c=0.5% in CHCl$_3$)

EXAMPLE 33

4-Bromodifluoromethoxy-2,3,5,6-tetrafluoro-benzyl 1R [1α 3α (E)]-2,2-dimethyl-3-(2-fluoro-3-methoxy-3-oxo-1-pro penyl)-cyclopropanecarboxylate with a specific rotation of $[\alpha]_D = +7° \pm 1°$ (c=1% in CHCl$_3$)

EXAMPLE 34

4-Methoxymethyl-2,3,5,6-tetrafluoro-benzyl 1R [1α 3α (E)]-2,2-dimethyl-3-(2-fluoro-3-ethoxy-3-oxo-1-propenyl) cyclopropanecarboxylate with a specific rotation of $[\alpha]_D = +7.5° \pm 1°$ (c=1% in CHCl$_3$)

EXAMPLE 35

4-Methoxymethyl-2,3,5,6-tetrafluoro-benzyl 1R [1α 3α (Z)]-2,2,-dimethyl-3-(3-methoxy-3-oxo-1-propenyl)- cyclo propanecarboxylate with a specific rotation of $[\alpha]_D = +23° \pm 1°$ (c=1% in CHCl$_3$)

EXAMPLE 36

4-Methoxymethyl-2,3,5,6-tetrafluoro-benzyl 1R [1α, 3α (E)]-2,2-dimethyl-3-[3-(1,1-dimethylethoxy)-2-fluoro-3-oxo-1-propenyl]-cyclopropanecarboxylate with a specific rotation of $[\alpha]_D = +19.5° \pm 1°$ (c=1% in CHCl$_3$)

EXAMPLE 37

4-Methoxymethyl-2,3,5,6-tetrafluoro-benzyl 1R [1α, 3 α (E)]-2,2-dimethyl-3-(2-fluoro-3-methoxy-3-oxo-1-propenyl)cyclopropanecarboxylate with a specific rotation of $[\alpha]_D=7°\pm2°$ (c=0.5% in CHCl$_3$)

EXAMPLE 38

4-(2-Propenyl)-2,3,5,6-tetrafluoro-benzyl 1R [1α, 3 α (E)]-2,2-dimethyl-3-(3-ethoxy-2-fluoro-3-oxo-1-propenyl)cyclopropanecarboxylate with a specific rotation of $[\alpha]_D=11.5°\pm2°$ (c=0.5% in toluene)

EXAMPLE 39

4-(2-Propenyl)-2,3,5,6-tetrafluoro-benzyl 1R [1α, 3α (Z)]-2,2-dimethyl-3-[3-[2,2,2-trifluoro-1-(trifluoromethyl) ethoxy]-3-oxo-1-propenyl]-cyclopropanecarboxylate melting at 58° C. and with a specific rotation of $[\alpha]_D=+5.5°\pm1°$ (c=1% in CHCl$_3$)

EXAMPLE 40

4-(2-Propynyl)-2,3,5,6-tetrafluoro-benzyl 1R [1α, 3 α (E)]-2,2-dimethyl-3-[2-fluoro-3-(1,1-dimethylethoxy)-3-oxo-1-propenyl]-cyclopropanecarboxylate with a specific rotation of $[\alpha]_D=+16.5°\pm1°$ (c=1% in CHCl$_3$)

EXAMPLE 41

4-(2-Propynyl)-2,3,5,6-tetrafluoro-benzyl 1R [1α, 3α (E)]-2,2-dimethyl-3-(2-fluoro-3-methoxy-3-oxo-1-propenyl)cyclopropanecarboxylate with a specific rotation of $[\alpha]_D=8°\pm1°$ (c=1% in CHCl$_3$)

EXAMPLE 42

4-(1,2-Propadienyl)-2,3,5,6-tetrafluoro-benzyl 1R [1α, 3α (E)]-2,2-dimethyl-3-[2-fluoro-3-(1,1-dimethylethoxy)-3- oxo-1-propenyl]cyclopropanecarboxylate with a specific rotation of $[\alpha]_D=+9.5°\pm1°$ (c=1% in CHCl$_3$)

EXAMPLE 43

4-(1,2-propadienyl)-2,3,5,6-tetrafluoro-benzyl 1R [1α, 3α (E)]-2,2-dimethyl-3-(2-fluoro-3-methoxy-3-oxo-1propenyl)-cyclopropanecarboxylate with a specific rotation of $[\alpha]_D=+2°\pm1°$ (c=1% in CHCl$_3$)

EXAMPLE 44

2,3,5,6-tetrafluoro-benzyl 1R [1α, 3α (E)]-2,2-dimethyl-3-(2-fluoro-3-methoxy-3-oxo-1-propenyl)-cyclopropane-carboxylate melting at 83° C. and with a specific rotation of $[\alpha]_D=+19.5°\pm1°$ (c=1% toluene)

EXAMPLE 45

4-Cyano-2,3,5,6-tetrafluoro-benzyl 1R [1α, 3α (E)]-2,2-dimethyl-3-[3-(1,1-dimethylethoxy)-2-fluoro-3-oxo-1-propenyl]-cyclopropanecarboxylate melting at 87° C. and with a specific rotation of $[\alpha]_D=+14°\pm1°$ (c=1% in CHCl$_3$)

EXAMPLE 46

4-Cyano-2,3,5,6-tetrafluoro-benzyl 1R [1α, 3α (E)]-2,2-dimethyl-3-(2-fluoro-3-methoxy-3-oxo-1-propenyl)-cyclopropanecarboxylate with a specific rotation of $[\alpha]_D=+13°\pm1°$ (c=1% CHCl$_3$)

EXAMPLE 47

4-Phenyl-2,3,5,6-tetrafluoro-benzyl 1R [1α, 3α (E)]-2,2-dimethyl-3-(3-ethoxy-2-fluoro-3-oxo-propenyl)-cyclopropanecarboxylate melting at <50° C. and with a specific rotation of $[\alpha]_D=-12°\pm2°$ (c=0.5% in CHCl$_3$)

EXAMPLE 48

4-Phenyl-2-3,5,6-tetrafluoro-benzyl 1R [1α, 3α(E)]-2,2-dimethyl-3-[3-(1,1-dimethylethoxy)-2-fluoro-3-oxo-propenyl]-cyclopropanecarboxylate melting at 90° C. and with a specific rotation of $[\alpha]_D=-5.5°\pm1°$ (c=1% in CHCl$_3$)

EXAMPLE 49

4-Benzyl-2,3,5,6-tetrafluoro-benzyl 1R [1α, 3α (E)]-2,2-dimethyl-3-(2-fluoro-3-methoxy)-3-oxo-1-propenyl)-cyclopropanecarboxylate with a specific rotation of $[\alpha]_D=+5°\pm1°$ (c=0.8% in CHCl$_3$)

EXAMPLE 50

4-benzyl- [2,3,5,6-tetrafluoro-benzyl 1R [1α, 3α (E)]-2,2-dimethyl-3-[3,(1,1- dimethylethoxy)-2-fluoro-3-oxo-1-propenyl]-cyclopropane carboxylate melting at 108° C. and with a specific rotation of $[\alpha]_D=+7.5°\pm1°$ (c=1% in CHCl$_3$)

EXAMPLE 51

4-Methyl-2,3,5,6-tetrafluoro-benzyl 1R [1α, 3α (Z)]-2,2-dimethyl-3-[[3((2,2,2-trifluoro-1-trifluoromethyl)-ethoxy]-3-oxo-1-propenyl]-cyclopropanecarboxylate melting at <50° C. and with a specific rotation of $[\alpha]_D=+8°\pm1°$ (c=1% CHCl$_3$)

EXAMPLE 52

4-methyl-2,3,5,6-tetrafluoro-benzyl 1R [1α, 3α (E)]-2,2-dimethyl-3-(2-fluoro-3-methoxy-3-oxo-1-propenyl)-cyclopropanecarboxylate with a specific rotation of $[\alpha]_D=+4°\pm2°$ (c=0.7% in CHCl$_3$)

EXAMPLE 53

4-Methyl-2,3,5,6-tetrafluoro-benzyl 1R [1α, 3α (E)]-2,2-dimethyl-3-(2-fluoro-3-butoxy-3-oxo-1-propenyl)-cyclopropanecarboxylate STEP A: 4-Methyl-2,3,5,6-tetrafluoro-benzyl 1R [1α, 3α(E)]-2,2-dimethyl-3-(2-fluoro-3hydroxy-3-oxo-1-propenyl)-cyclopropanecarboxylate 3.85 g of the product of Example 9 were heated for 1 hour at 130° C. in 38.5 ml of toluene in the presence of 0.385 g of p-toluenesulfonic acid. The mixture was allowed to return to ambient temperature, was washed with water and dried. The solvents were evaporated under reduced pressure to obtain 3.75 g of expected product melting at ≃90°–95° C.

STEP B: 4-Methyl-2,3,5,6-tetrafluoro-benzyl 1R [1α3α (E)]-2,2-dimethyl-3-(2-fluoro-3-butoxy-3-oxo-1-propenyl)-cyclopropanecarboxylate Treating the product of Step A with butanol in methylene chloride in the presence of dicyclohexylcarbodiimide and dimethylaminopyridine, the expected product was obtained with a specific rotation of $[\alpha]_D=-32.5°\pm2°$ (c=0.5% in CHCl$_3$) Operating in the same way using the appropriate alcohol, the following products were prepared.

EXAMPLE 54

4-Methyl-2,3,5,6-tetrafluoro-benzyl 1R [1α, 3α(E)]-2,2-dimethyl-3-(2-fluoro-3-propoxy-3-oxo-1-propenyl)-cyclopropanecarboxylate with a specific rotation of $[\alpha]_D=-19.5°\pm2°$ (c=0.4% in CHCl$_3$)

EXAMPLE 55

4-Methyl-2,3,5,6-tetrafluoro-benzyl 1R [1α, 3α (E)]-2,2-dimethyl-3-[2-fluoro-3-(1-methyl)-ethoxy-3-oxo-1-propenyl]cyclopropanecarboxylate with a specific rotation of $[\alpha]_D = -4° \pm 2°$ (c=0.6% in CHCl$_3$)

EXAMPLE 56

4-Hydroxy-2,3,5,6-tetrafluoro-benzyl 1R [1α, 3α(E)]-2,2-dimethyl-3-(3-ethoxy-2-fluoro-3-oxo-1-propenyl)-cyclopropanecarboxylate

STEP A:
4-[Dimethyl-(1,1-dimethyl)-ethylsiloxy]-2,3,5,6-tetrafluoro-benzyl 1R [1α, 3α
(E)]-2,2-dimethyl-3-(3-ethoxy-2-fluoro-3-oxo-1-propenyl)-cyclopropanecarboxylate. The reaction was The reaction was carried out as in Example 1, starting with the suitable acid and alcohol to obtain the expected product. IR Spectrum (CHCl$_3$): Aromatic: 1656 - 1515 - 1497 cm$^{-1}$ C=O: 1727 cm$^{-1}$

STEP B: 4-Hydroxy-2,3,5,6-tetrafluoro-benzyl 1R [1α, 3α
(E)]-2,2-dimethyl-3-(3-ethoxy-2-fluoro-3-oxo-1-propenyl)-cyclopropanecarboxylate 1.8 g of the product of Step A in 5 ml of tetrahydrofuran were cooled to 4° C. and 3.5 ml of a solution (1M) of tetrabutyl ammoniumfluoride in tetrahydrofuran were added over the course of 5 minutes. The mixture was stirred for 30 minutes, poured into an ice-cold aqueous ammonium chloride solution, extracted with ether, washed with water, and the solvent removed under reduced pressure. After chromatography on silica (eluent 1:1 hexane:ethyl acetate), the expected product was obtained with a specific rotation of $[\alpha]_D = +5.5° \pm 1°$ (c=0.8% in CHCl$_3$)

Preparation 1: α methyl-2,3,5,6-tetrafluoro-benzyl alcohol 3 2 ml of methyl iodide were introduced over the course of 30 minutes into a suspension of 1 g of magnesium and 30 ml of ethyl ether and the mixture was stirred for 30 minutes. The mixture was cooled to 0° C. and 4 g of 4-methyl-2,3,5,6-tetra fluorobenzaldehyde and 100 ml of ethyl ether were introduced over the course of 30 minutes. The reaction mixture was stirred for 1 hour at 0° C. and was poured into 150 ml of a saturated aqueous ammonium chloride solution. Extraction was carried out with ether and the ethereal phases were dried and evaporated to dryness under reduced pressure. The crude product was chromatographed on silica and eluted with a hexane:isopropyl ether (8:2) mixture to obtain 3.85 g of the product with a Rf=0.10.

Preparation 2: α-cyano-4-methyl-2,3,5,6-tetrafluoro-benzyl alcohol 1.66 g of sodium cyanide were introduced into a mixture of 4 g of 4-methyl-2,3,5,6-tetrafluorobenzaldehyde, 4 g of 4-methyl-2,3,5,6-tetrafluorobenzaldehyde, 70 ml of methyl alcohol and 20 ml of water and the mixture was cooled to 0° C. The reaction mixture was stirred for 1 hour at 0° C. and was poured into water. Extraction was carried out with ether and the ethereal phases were dried and evaporated to dryness under reduced pressure to obtain 4.54 g of the product melting at 124° C.

Preparation 3: 2,3,5,6-tetrafluoro-4-(hydroxymethyl)benzonitrile

STEP A-:
2,3,5,6-Tetrafluoro-4-[[(tetrahydropyran-2-yl)oxy]methyl]-benzaldehyde.

13 g of 2-[(2,3,5,6-tetrafluorophenyl)-methoxy]-tetrahydropyran in 200 ml of tetrahydrofuran were cooled to −60 C. and 35.1 ml of butyllithium (1,6M) in hexane were added dropwise over the course of 30 minutes. The mixture was stirred for 1 hour at −55° C. and 5 ml of dimethylformamide dissolved in 10 ml of tetrahydrofuran were added over the course of 5 minutes. The mixture was stirred for ½hours at this temperature and 50 ml of a saturated aqueous sodium chloride solution were added. Extraction was carried out with isopropyl ether and the extract was dried and the solvents removed under reduced pressure to obtain 14.4 g of the expected product which was used as is in the following step.

STEP B:
2,3,5,6-Tetrafluoro-4-(hydroxymethyl)benzonitrile 11.7 g of the aldehyde of Step A and 6.8 g of sodium acetate trihydrate were dissolved in 100 ml of methanol and 4.2 g of ammonium chloride were then added. The mixture was poured into water and extracted with isopropanol. The extract was dried and the solvents removed under reduced pressure to obtain 13.6 g of the oxime melting at 130° C. The product obtained was heated at reflux for 4 hours in 400 ml of acetonitrile in the presence of 1.6 g of cuprous acetate and was then cooled to 40° C. and concentrated to dryness. The residue was taken up again with 300 ml of isopropanol, washed with water and then with salted water, dried and the solvents removed under reduced pressure to obtain 11.3 g of the nitrile-containing product. 0.625 g of p-toluenesulfonic acid were added to 12.5 g of the said product in 62.5 ml of methanol, stirred for 1 hour at ambient temperature, poured into ice-cold water, extracted with isopropanol, washed with water and then with salted water, dried and the solvents removed under reduced pressure to obtain 11.5 g of 2,3,5,6-tetrafluoro-4-(hydroxymethyl)benzonitrile melting at 50° C.

Preparation 4: 4-[(1,1-dimethylethyl)-dimethylsilyloxy]-2,3,5,6-tetrafluorobenzyl alcohol

STEP A
[1-(Tetrahydro-2H-pyran-2-yl)oxy]-2,3,5,6-tetrafluoro-4[(2-tetrahydropyranyloxy)-methyl]-phenol 8.4 g of potassium hydroxide were added to a solution of 15.3 g of the pyranyl derivative of pentafluorobenzyl alcohol in 140 ml of tert-butanol and the mixture was refluxed for 4 178 hours. The mixture was allowed to return to ambient temperature and an ice-cold saturated aqueous sodium hydrogen phosphate solution was added. The mixture was extracted with ethyl acetate, washed with water and then with salted water, dried and the solvents removed under reduced pressure to obtain 16 g of the cooled product which was chromatographed on silica (eluent: hexane:ethyl acetate: 7:3) to obtain 10.78 g of expected product melting at 90° C.

STEP B:
2-[[4-[(1,1-dimethylethyl)dimethylsilyloxy]-2,3,5,6-tetrafluorophenyl]-methoxy]tetrahydropyran 2 8 g of the product of Step A dissolved in 14 ml of tetrahydrofuran were cooled to 4° C. and 1.7 ml of triethylamine were added. A solution of 1.8 g of tert-butyl dimethylsilyl chloride in 6 ml of tetrahydrofuran were then added over the course of 15 minutes and the mixture was stirred for 40 minutes, filtered and the solvent removed. The residue was taken up with isopropanol and filtered to obtain 4 g of 4-[(1,1-dimethylethyl)dimethylsilyloxy]-2,3,5,6-tetrafluorobenzyl alcohol.

STEP C: 4-[(1,1-dimethylethyl)-dimethylsilyloxy]-2,3,5,6-tetrafluorobenzyl alcohol.

0.1 g of p-toluenesulfonic acid was added at ambient temperature to solution of 2 g of the product of Step B in 10 ml of methanol. The mixture is stirred for 1 hour, poured into ice-cold water, extracted with ether and the solvent removed under reduced pressure. After chromatography of the residue on silica (eluent: methylene chloride), 1.16 g of expected product were obtained.

Preparation 5:
4-bromodifluoromethoxy-2,3,5,6-tetrafluoro-benzyl alcohol prepared by the following reaction scheme:

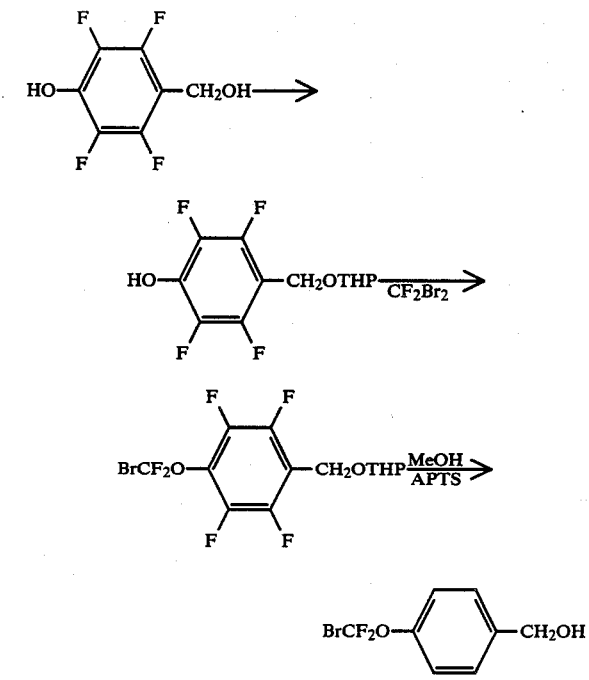

Preparation 6:
4-difluoromethoxy-2,3,5,6-tetrafluorobenzyl alcohol prepared by the following reaction scheme:

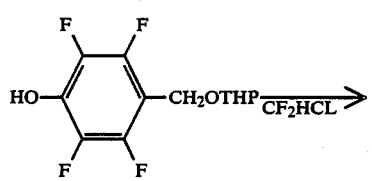

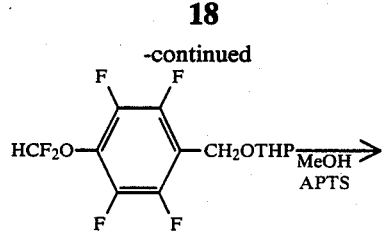

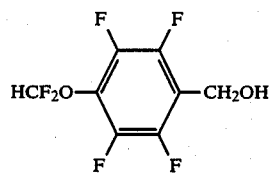

Preparation 7:
2-[[2,3,5,6-tetrafluoro-4-(1,2-propadienyl)-phenyl]-methoxy]-tetrahydropyran prepared by the reaction scheme below:

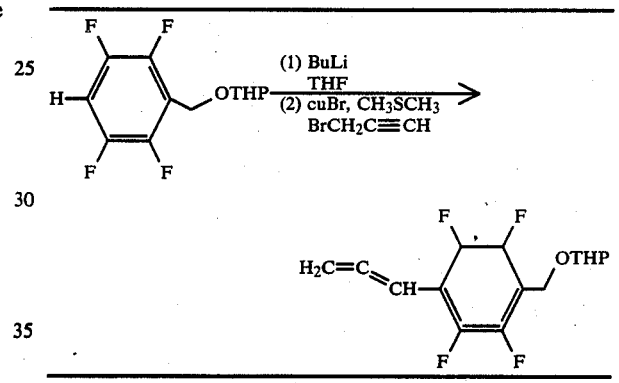

| Example 57: Preparation of a soluble concentrate A homogeneous mixture of the following were prepared: | |
|---|---|
| Product of Example 8: | 0.25 g |
| Piperonyl butoxide: | 1.00 g |
| Tween 80: | 0.25 g |
| Topanol A | 0.1 g |
| Water: | 98.4 g |
| Example 58: Preparation of an emulsifiable concentrate The following were intimately mixed: | |
| Product of Example 9: | 0.015 g |
| Piperonyl butoxide: | 0.5 g |
| Topanol A: | 0.1 g |
| Tween 80: | 3.5 g |
| Xylene: | 95.885 g |
| Example 59: Preparation of an emulsifiable concentrate A homogeneous mixture of the following was prepared: | |
| Product of Example 34: | 1.5 g |
| Tween 80: | 20.00 g |
| Topanol A: | 0.1 g |
| Xylene: | 78.4 g |
| Example 60: Preparation of a smoke-producing composition The following were homogeneously mixed: | |
| Product of Example 36: | 0.25 g |
| Tabu powder: | 25.00 g |
| Cedar Leaf powder: | 40.00 g |
| Pine wood dust: | 33.75 g |
| Brilliant green: | 0.5 g |
| Para-nitrophenol: | 0.5 g |

BIOLOGICAL STUDY

A. Knockdown effect on house fly

The test insects were 4 day old female house flies and the test was carried out by direct spraying at a concentration of 0.25 g/l in a Kearns and March chamber using a mixture of acetone (5%) and Isopar L (petroleum solvent) as solvent (quantity of solvent employed: 2 ml in one second). 50 insects were used per treatment and observations were made every minutes up to 10 minutes, and then at 15 minutes and the $KT_{50}$ was determined by the usual methods. The experimental results obtained are summarized in the following table:

| Compound | $KT_{50}$ in min. |
|---|---|
| Example 9 | 5.8 at 1 g/l |
| Example 8 | 6.5 at 100 mg/l |
| Example 34 | 1.54 at 100 mg/l |
| Example 36 | 2.611 at 1 g/l |
| Example 38 | 4.5 at 1 g/l |

B. Study of the Lethal effect on various insects (a) Lethal ffect on houseflies

The test insects were 4 to 5 day-old female house flies and the study was carried out by local application of 1μ of a solution in acetone onto the dorsal thorax of insects using an Arnold micromanipulator. 50 individuals were employed per treatment and moraltity was recorded 24 hours after treatment. The results obtained, expressed as $LD_{50}$ or dose (in nanograms) per individual required to kill 50% of the insects, are as follows:

| Compound | $LD_{50}$ in ng/insect |
|---|---|
| Example 9 | 25 |
| Example 8 | 19 |
| Example 34 | 8.8 |
| Example 36 | 13.7 |
| Example 38 | 3.34 |

(b) Lethal effect on cockroaches

The tests were carried out by film contact on glass by depositing solutions of different concentrations in acetone with a pipette onto the bottom of a glass Petri dish, the edges of which were previously dusted with chalk to prevent the insects from escaping. The lethal concentration 50 ($LC_{50}$) was determined. The experimental results obtained are summarized in the following table:

| Compound | $LC_{50}$ in mg/m$^2$ |
|---|---|
| Example 9 | 0.22 |
| Example 8 | 0.33 |

(c) Lethal effect on *Spodoptera Littoralis* Larvae

The tests were carried out by local application of a solution in acetone using an Arnold micromanipulator onto the dorsal thorax of the larvae. 15 larvae were employed per dose of product to be tested and the larvae employed were larvae of the fourth larval stage, i.e. approximately 10 days old when they were reared at 24° C. and 65% relative humidity. After treatment, the individuals were placed in an artificial nutrient medium (Poitout medium) and mortalities were recorded hours after treatment. The experimental results obtained are summarized in the following table:

| Compounds | $LD_{50}$ in ng per insect |
|---|---|
| Example 9 | 11.5 |

(d) Lethal effect on *Aphis cracivora*

7day-old adults were employed and 10 Aphis were used per concentration employed. A contact-ingestion method was employed wherein a broadbean leaf was treated using a Fisher gun and the leaf was placed on a moist paper disc in a plastic Petri dish. The treatment was carried out using 2 ml of the solution in acetone of the product to be tested (1 ml per side of the leaf). Infestation by the insect was carried out after drying the leaf and the insects were maintained in contact with the leaf for 1 hour. The insects were placed on untreated leaves and the mortality was recorded after 24 hours. The experimental results obtained are summarized in the following table:

| Compounds | $LD_{50}$ in ng/insect |
|---|---|
| Example 9 | 0.5 |
| Example 8 | 1.6 |
| Example 34 | 0.716 |
| Example 36 | 1.665 |
| Example 38 | 0.485 |

C. Acaricidal activity

Bean seedlings carrying 2 leaves infested with 25 *Tetranychus urticae* females per leaf and placed under an aerated dome below a constant light luminous ceiling were employed The seedlings were treated using a Fischer gun with 4 ml of toxic solution per seedling of a mixture of water and acetone at equal volumes. The solution was allowed to dry for 12 hours and infestation was carried out. Observations on mortality were made 80 hours later and the dose employed in each test was 5 g of product per hl. The lethal concentration 50 ($LC_{50}$) was determined. The experimental results are as follows:

| Compounds | $LC_{50}$ in mg/l |
|---|---|
| Example 9 | 75 |
| Example 8 | 500 |
| Example 34 | 244.3 |
| Example 36 | 2.278 |
| Example 38 | 185.4 |

Various modifications of the products and methods of the invention may be made without departing from the spirit or scope thereof and it should be understood that the invention is intended to be limited only as defined in the appended claims.

What we claim is:

1. Cyclopropane carboxylic acid esters of all possible stereoisomeric forms and mixtures thereof of the formula

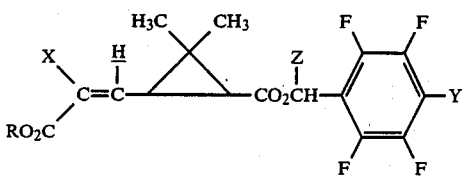

wherein X is selected from the group consisting of hydrogen and fluorine, R is selected from the group consisting of alkyl of 1 to 8 carbon atoms and alkenyl of 2 to 8 carbon atoms unsubstituted or substituted with fluorine and, Z is selected from the group consisting of hydrogen, —CH$_3$ and —C≡CH and Y is selected from the group consisting of hydrogen, —OH, alkyl of 1 to 8 carbon atoms and alkenyl of 2 to 8 carbon atoms either being unsubstituted or substituted with halogen —CN, —(CH$_2$)$_m$—OAlk and —(CH$_2$)$_m$—S—Alk, m is 0, 1, 2, 3 or 4, Alk is alkyl of 1 to 12 carbon atoms.

2. A compound of claim 1 wherein X is fluorine.
3. A compound of claim 1 wherein X is hydrogen.
4. A compound of claim 1 wherein R is alkyl of 1 to 4 carbon atoms.
5. A compound of claim 1 wherein Z is hydrogen.
6. A compound of claim 1 wherein Y is —CH$_3$, —CH$_2$—CH=CH$_2$ or —(CH$_2$)$_m$—OCH$_3$ and m is 0 or 1.
7. A compound of claim 1 selected from the group consisting of 4-methoxy-2,3,5,6-tetrafluoro-benzyl 1R [1α, 3α (Z)]-2,2-dimethyl-3-(3-methoxy-3-oxo-1-propenyl)-cyclopropane carboxylate; 4-methyl-2,3,5,6-tetrafluoro-benzyl 1R [1α, 3α (E)]-2,2-dimethyl-3-(2-fluoro-3-ethoxy-3-oxo-1-propenyl)cyclo propanecarboxylate; 4-methyl-2,3,5,6-tetrafluoro-benzyl 1R [1α, 3α (E)]-2,2-dimethyl -3-[3-(1,1-dimethylethoxy)-3-oxo-2-fluoro-1-propenyl]-cyclopropanecarboxylate; 4-(2-propenyl)-2,3,5,6-tetrafluoro-benzyl 1R [1α, 3α(E)]-2,2-dimethyl-3-(3-ethoxy-2-fluoro-3-oxo1propenyl)-cyclopropane carboxylate; 4-methoxy-2,3,5,6-tetrafluoro-benzyl 1R [1α, 3α (E)]-2,2-dimethyl-3-[2-fluoro-3-(1,1-dimethylethoxy-3-oxo-1-propenyl]cyclopropanecarboxylate; 4-methoxy-2,3,5,6-tetrafluoro-benzyl 1R [1α, 3α (E)]-2,2-dimethyl-3-(2-fluoro-3-ethoxy-3-oxo-1-propenyl)-cyclopropane carboxylate; 4-methoxymethyl-2,3,5,6-tetrafluoro-benzyl 1R [1α, 3α (E)]]-2,2-dimethyl-3-(2-fluoro-3-ethoxy-3-oxo-1-propenyl)-cyclo propanecarboxylate; 4-methoxymethyl-2,3,5,6-tetrafluoro-benzyl 1R [1α, 3α, (E)]]-2,2-dimethyl-3-[3-(1.1-dimethyl-ethoxy-2-fluoro-3-oxo-1-propenyl]-cyclopropanecarboxylate; and 4-methoxymethyl 2,3,5,6-tetrafluoro-benzyl 1R [1α, 3α, (E)]-2,2-dimethyl-3-[2-fluoro-3-methoxy-3-oxo-1-propenyl)-cyclopropancarboxyl ate.

8. An acaricidal composition comprising an acaricidally effective amount of at least one compound of claim 1 and an inert carrier.
9. A composition of claim 8 wherein X is fluorine.
10. A composition of claim 8 wherein X is hydrogen.
11. A composition of claim 8 wherein R is alkyl of 1 to 4 carbon atoms.
12. A composition of claim 8 wherein Z is hydrogen.
13. A composition of claim 12 wherein Y is —CH$_3$, —CH$_2$—CH=CH$_2$ or —(CH$_2$)$_m$—OCH$_3$ and m is 0 or 1.
14. A composition of claim 8 wherein the active compound is selected from the group consisting of 4-methoxy-2,3,5,6-tetrafluoro-benzyl 1R [1α, 3α (Z)]-2,2-dimethyl-3-(3-methoxy-3-oxo-1-propenyl)-cyclopropanecarboxylate; 4-methyl-2,3,5,6-tetrafluoro-benzyl 1R [1α, 3α(E)]-2,2-dimethyl-3-(2-fluoro-3-ethoxy-3-oxo-1-propenyl)-cyclopropanecarboxylate; 4-methyl-2,3,5,6-tetrafluoro-benzyl 1R [1α, 3α (E)]-2,2-dimethyl-3-[3-(1,1-dimethylethoxy)-3-oxo-2-fluoro-1-propenyl]-cyclopropanecarboxylate; 4-(2-propenyl)-2,3,5,6-tetrafluoro-benzyl 1R, (1α, 3α ) (E)]-2,2-dimethyl-3-(3-ethoxy-2-fluoro-3-oxo-1-propenyl)-cyclopropane carboxylate; 4-methoxy-2,3,5,6-tetrafluoro-benzyl 1R [1α, 3α (E)]-2,2-dimethyl-3-[2-fluoro-3-(1,1-dimethyl)-ethoxy-3-oxo-1-propenyl]-cyclopropanecarboxylate; 4-methoxy-2,3,5,6-tetrafluoro-benzyl 1R [1α, 3α (E)]-2,2-dimethyl-3-(2-fluoro-3-ethoxy-3-oxo-1-propenyl-cyclopropane-carboxylate; 4-methoxymethyl-2,3,5,6-tetrafluoro-benzyl 1R [1α, 3α, (E)]]-2,2-dimethyl-3-(2-fluoro-3-ethoxy-3-oxo-1-propenyl)-cyclopropane carboxylate; 4-methoxymethyl-2,3,5,6-tetrafluoro)-benzyl 1R [1α, 3α (E)]]-2,2-dimethyl-3-[3-(1,1-dimethylethoxy-2-fluoro-3-oxo-1-propenyl-cyclopropanecarboxylate; and 4-methoxymethyl-2,3,5,6-tetrafluoro-benzyl 1R [1α, 32 α (E)]-2,2,-dimethyl-3-[2-fluoro-3-methoxy-3-oxo 1-propenyl)-cyclopropanecarboxylate.

15. A method of combatting nematodes comprising contacting nematodes with a nematocidally effective amount of at least one compound of claim 1.
16. A method of combatting acariens comprising contacting acariens with an acaricidally effective amount of at least one compound of claim 1.
17. A method of combatting insects comprising contacting insects with an insecticidally effective amount of at least one compound of claim 1.
18. A method of claim 17 wherein X is fluorine.
19. A method of claim 17 wherein X is hydrogen.
20. A method of claim 17 wherein R is alkyl of 1 to 4 carbon atoms.
21. A method of claim 17 wherein Z is hydrogen.
22. A method of claim 17 wherein Y is —CH$_3$, —CH$_2$—CH=CH$_2$ or —(CH$_2$)$_m$—OCH$_3$ and m is 0 or 1.
23. A method of claim 17 wherein the active compound is selected from the group consisting of 4-methoxy-2,3,5,6-tetrafluoro-benzyl 1R [1α, 3α (Z)]-2,2-dimethyl-3-(3-methoxy-3-oxo-1-propenyl)-cyclopropanecarboxylate; 4-methyl-2,3,5,6-tetrafluoro-benzyl 1R [1α, 3α (E)]-2,2-dimethyl-3-(2-fluoro-3-ethoxy-3-oxo-1-propenyl)-cyclopropane-carboxylate; 4-methyl-2,3,5,6-tetrafluoro-benzyl 1R [1α, 3α (E)]-2,2-dimethyl-3-[3-(1,1-dimethylethoxy)-3-oxo-2-fluoro-1-propenyl]cyclopropanecarboxylate; 4-(2-propenyl)-2,3,5,6-tetrafluoro-benzyl 1R (1α, 3α ) (E)],-2-dimethyl-3-(3-ethoxy-2-fluoro-3-oxo-1-propenyl)-cyclopropanecarboxylate; 4-methoxy-2,3,5,6-tetrafluoro-benzyl 1R [1α, 3α (E)]-2,2-dimethyl-3-[2-fluoro-3-(1,1-dimethylethoxy-3-oxo-1-propenyl]cyclopropanecarboxylate; 4-methoxy-2,3,5,6-tetrafluoro-benzyl 1R [1α, 3α (E)]-2,2-dimethyl-3-(2-fluoro-3-ethoxy-3-oxo-1-propenyl)-cyclopropane-carboxylate; 4- methoxymethyl-2,3,5,6-tetrafluoro-benzyl 1R [1α, 3α (E)]]-2,2-dimethyl-3-(2-fluoro-3-ethoxy-3-oxo-1-propenyl)-cyclopropane-carboxylate; 4-methoxymethyl-2,3,5,6-tetrafluoro-benzyl 1R [1α, 3α (E)]]-2,2-dimethyl-3-[3(1,1 -dimethylethoxy-2-fluoro-3-oxo-1-propenyl]-cyclopropanecarboxylate; and 4-methoxymethyl-2,3,5,6-tetra-fluoro-benzyl [1R [1α, 3α (E)]-2,2-dimethyl-3-[2-fluoro-3-methoxy-3-oxo-1-propenyl]-cyclopropanecarboxylate.

* * * * *

UNITED STATES PATENT AND TRADEMARK OFFICE
CERTIFICATE OF CORRECTION

PATENT NO. : 4,939,172

DATED : July 3, 1990

INVENTOR(S) : JOSEPH CADIERGUE.; JACQUES DEMASSEY; JEAN-PIERRE DEMOUTE; and JEAN TESSIER It is certified that error appears in the above-identified patent and that said Letters Patent is hereby corrected as shown below:

Col.    Line 22    22                 "[1$\alpha$, 32$\alpha$" should be

Claim 14       --[1$\alpha$, 3$\alpha$--

Signed and Sealed this

Third Day of March, 1992

Attest:

HARRY F. MANBECK, JR.

*Attesting Officer*        *Commissioner of Patents and Trademarks*